United States Patent
Garvin

(12) 
(10) Patent No.: US 6,391,004 B1
(45) Date of Patent: May 21, 2002

(54) FLUID COLLECTOR ASSEMBLY

(75) Inventor: David M. Garvin, Coral Gables, FL (US)

(73) Assignee: Retrax Safety Systems, Inc., Miami, FL (US)

( * ) Notice: Subject to any disclaimer, the term of this patent is extended or adjusted under 35 U.S.C. 154(b) by 0 days.

(21) Appl. No.: 09/620,929

(22) Filed: Jul. 21, 2000

(51) Int. Cl.[7] .............................................. A61M 5/32
(52) U.S. Cl. ........................ 604/110; 604/195; 600/577
(58) Field of Search ................................ 604/110, 195, 604/198, 263, 192, 240, 291, 164.02; 600/576–579

(56) References Cited

U.S. PATENT DOCUMENTS 4,904,242 A * 2/1990 Kulli ...................... 600/576 X
5,403,286 A * 4/1995 Lockwood, Jr. ............ 604/110

* cited by examiner

Primary Examiner—Anhtuan T. Nguyen
(74) Attorney, Agent, or Firm—McHale & Slavin

(57) ABSTRACT

The present invention relates to a fluid collection method and assembly in which the needle is retracted inside the syringe after the sample is taken. A standard sealed blood collection tube is inserted into the outer barrel of the syringe. A double ended needle held by the syringe has one end inserted into the patient and the other end through the seal of the blood collection tube. After the blood collection tube is removed, the user inserts a plunger into the cavity between an inner and outer barrel which initiates an automatic retraction of the needle into the assembly device. In operation, a collet is expanded and a spring biased needle retractor is engaged in response to the forward movement of the plunger. The forward end of the barrel carries a wedge which force the collet to expand upon forward movement of the collet.

13 Claims, 7 Drawing Sheets

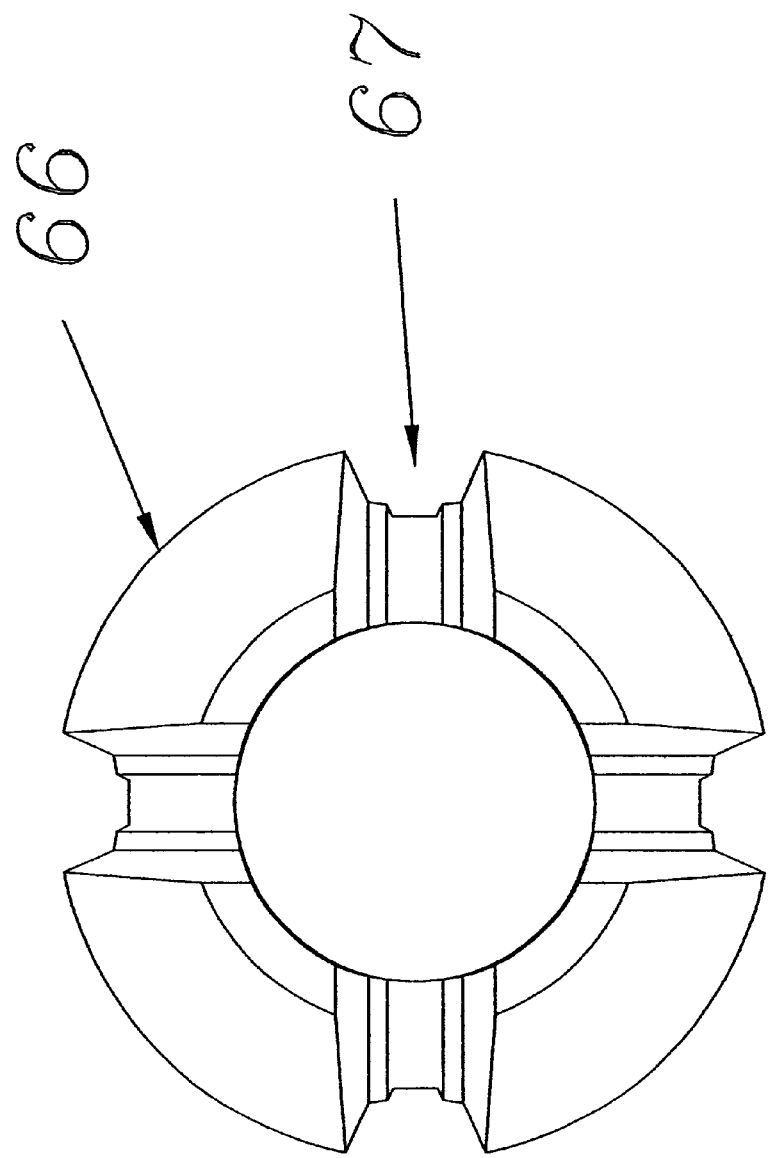

FLUID COLLECTOR ASSEMBLY

This application is related to U.S. Pat. No. 5,984,898 and pending application, Ser. No. 09/575,007 filed May 19, 2000 now U.S. Pat. No. 6,273,870.

FIELD OF THE INVENTION

This invention relates generally to the collection of blood samples and more specifically to a method and an assembly for collecting fluid samples with a retractable needle and fluid collecting tube holding device which following the stroke of the plunger, automatically retracts the needle into the body of the assembly.

BACKGROUND OF THE INVENTION

Blood samples and other medical specimens are routinely taken and collected in a specimen collection container. The typical blood collection container is a hollow blood collection tube with one end closed by a semi-spherical portion and the other end open. The open end is sealable by an impervious elastomeric cover.

To collect a blood sample, the tube is used in concert with a tube holding device. Normally the holding device has a hollow needle extending through the closed end of a tubular housing. The tubular housing has an opposed open end for accepting the blood collection tube. The hollow needle is inserted through the dermal layer into the lumen of the blood vessel into the circulation system of a subject to direct blood there through towards the interior compartment of the holding device. The collection container is inserted through the open end of the holder so that the hollow needle punctures through the elastomeric cover of the collection container. The interior of the collection container is now in direct communication with the circulation system and, having typically been formed in a vacuum, draws blood through the hollow needle and into the collection container. Once enough blood has been drawn, the container may be removed from the holder.

The tube holding device with its contaminated needle presents the danger of an accidental needle stick. Even trace amounts of body fluids from a person with Hepatitis, Acquired Immune Deficiency Syndrome (AIDS) etc. transferred into another's blood stream can transmit these diseases. Thus, what is needed in the art is a fluid collecting tube holding device that protects from inadvertent needle sticks.

SUMMARY OF THE INVENTION

Thus, an object of the instant invention is to provide a fluid collecting tube holder that causes the contaminated hypodermic syringe to retract into the holder, by insertion of a plunger, so that the needle is enclosed within the holder.

It is a further object of the instant invention to provide a plunger device that is either unattached or attached to the fluid colleting tube device holder such that it does not interfere with the collection of the fluid sample but is easily accessible for insertion into the tube holding device.

Another object of the instant invention is to provide a collet which expands and releases a spring biased needle retractor in response to the forward movement of the plunger. The forward end of the outer barrel carries a wedge which insures the collet fingers will spread apart upon forward movement of the collet.

It is yet another object of the instant invention to provide a vent in the plunger. The vent allows air to escape from the interior of the plunger as the needle assembly is retracted by or in response to spring action.

It is still another object of the instant invention is to provide an inexpensive, easily manufactured and used tube holding device with a retractable needle mechanism for safe disposal and prevention of diseases.

It is further objective of the instant invention to provide a method for collecting fluid samples that significantly reduces accidental needle sticks.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate objects and features thereof.

BRIEF DESCRIPTION OF THE DRAWINGS

FIG. 6 is an end view of the expanding collet used in the present invention;

DETAILED DESCRIPTION

Figure 1:
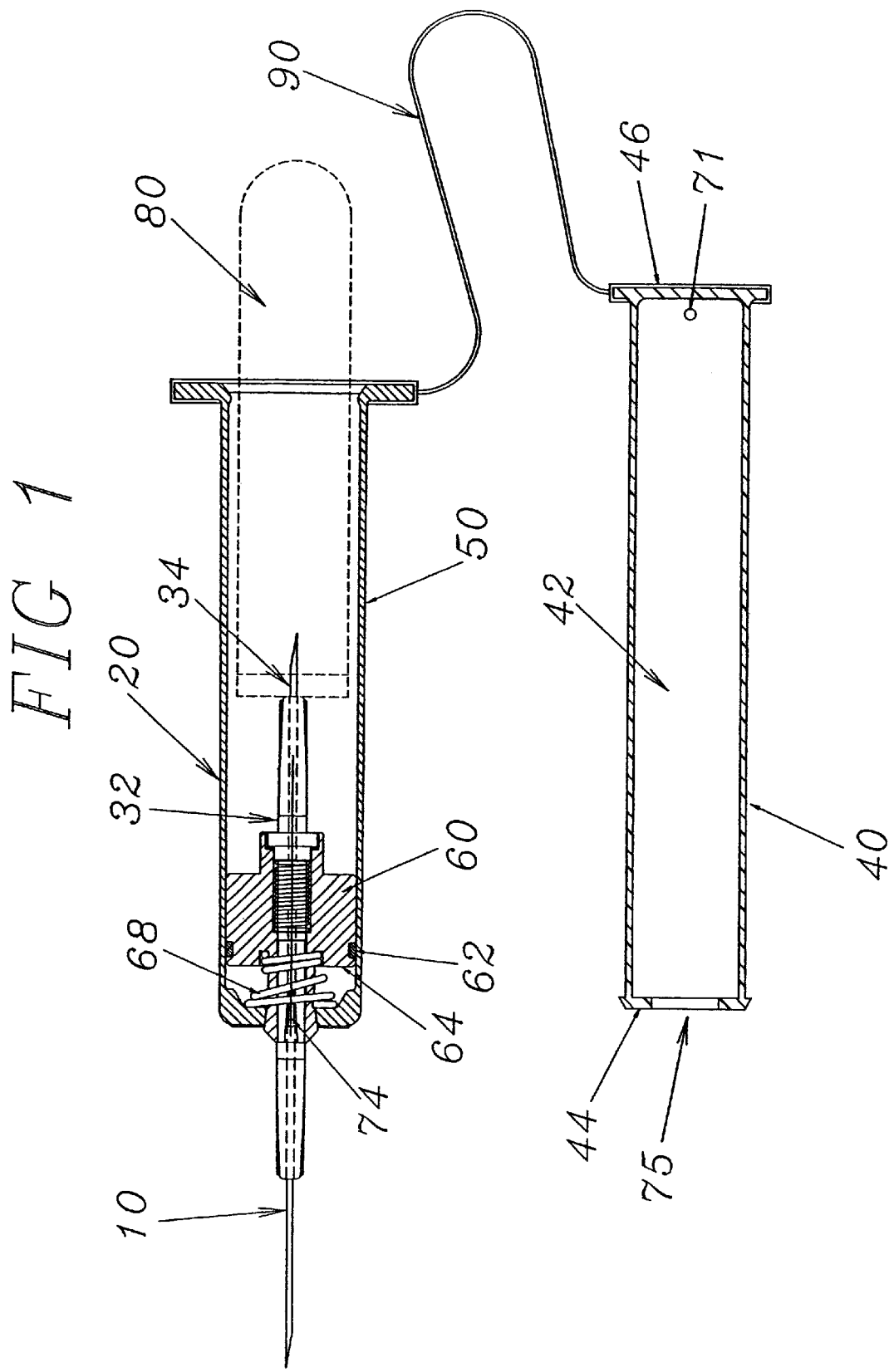
FIG. 1 is a partial sectional view of the fluid collection assembly.
Figure 2:
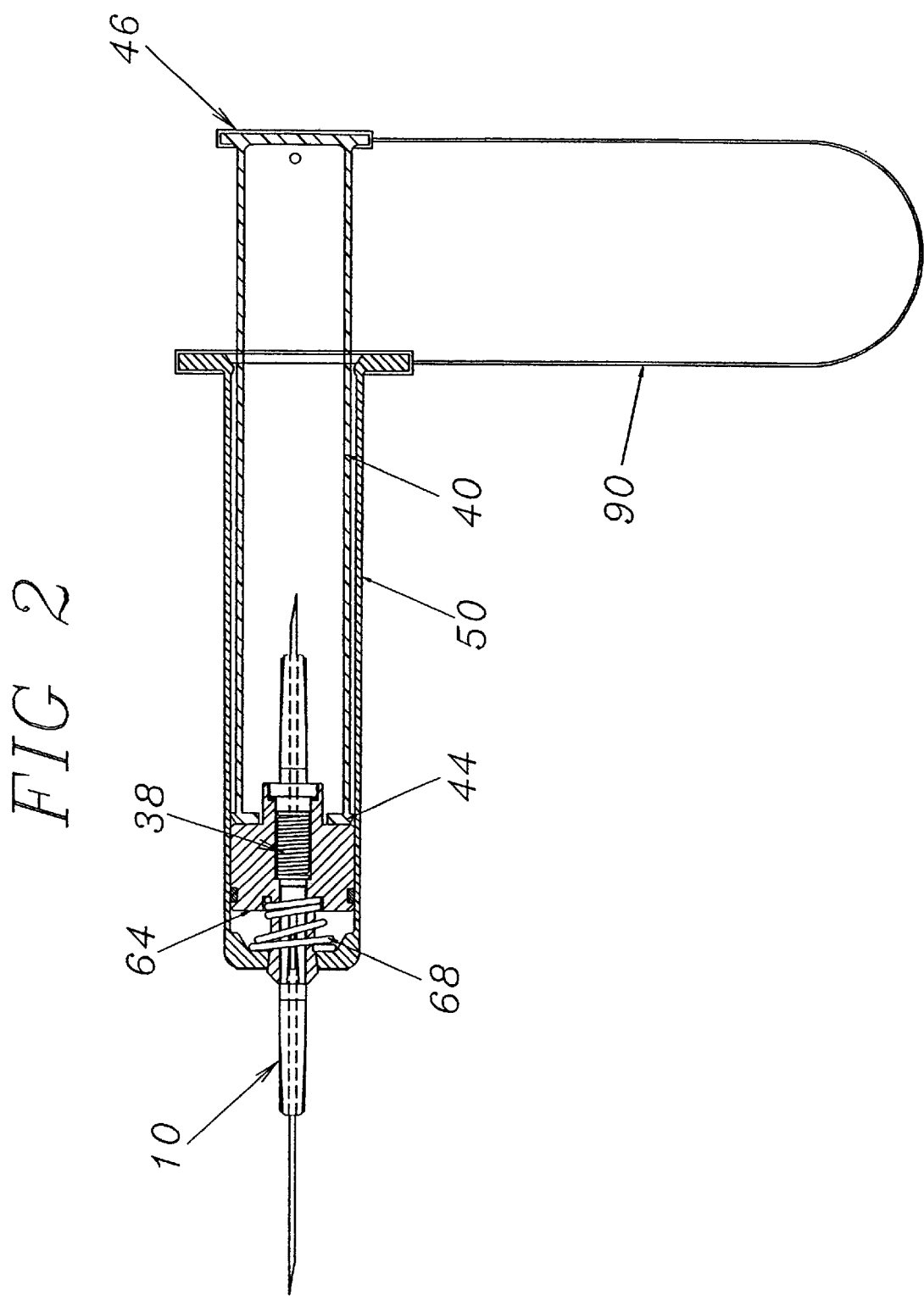
FIG. 2 is a partial sectional side view of the fluid collection assembly with the plunger in the forward position, a screw mounted needle according to the present invention is shown.

As shown in FIGS. 1–5, the invention is a combination of a fluid collection tube holding device 20 and a needle 10. The device features a separately attached needle hub including a metal cannula 12 and a threaded attachment portion 14.

The fluid collection tube holding device 20 includes a hollow inner barrel 60 which cooperates with a needle retractor 30 to draw the needle 10 into the inner barrel following use of the needle. This action is accomplished by inserting the plunger 40 into the hollow space between the inner barrel 60 and outer barrel 50. The continued stroke of the plunger 40 moves collet 66 forward and releases needle retractor 30 which is then propelled by spring action into the body of the plunger.

The fluid collection tube holding device 20 is made up of an outer barrel or tube 50 and an inner barrel 60. The inner barrel has a forward end 64 which has an additional seal element 62, O-ring in this embodiment, which seals the inner barrel to the inner surface of the outer barrel 50. Between the inner barrel 60 and the outer barrel 50 is a space into which the plunger 40 is introduced from the rear end of the syringe. The plunger 40 has a tubular body 42 and an annular plunger end 44 with a central aperture 75 on a forward end of the plunger. Aperture 75 is sized to accommodate the inner barrel 60. The annular plunger end 44 is sized to form liquid proof contact with the outer barrel. At the rear end of the plunger a push element 46 can be provided to engage the user's thumb. A vent 71 is formed in the rear end of the plunger adjacent to push element 46. The vent 71 permits outward flow of air from the interior of the plunger when the needle 10 and retractor 30 are retracted into the plunger.

The forward end 64 of the inner barrel 60 also includes a collet 66 which acts as a movable stop between the outer barrel and the needle retractor. The collet has slots 67 in the external funnel shape which creates a contracting and clamping effect for the collet as it is withdrawn through the opening 72 located at the forward end of the outer barrel 50. The collet is biased into a clamping or retracted position by a short spring 68 which biases the inner barrel 60 rearwardly with respect to the outer barrel 50.

The holder 30 is adapted to be inserted through the tubular body of the inner barrel 60 from a rearward end thereof. The retracting holder 30 includes a fluid expelling portion 32 with a puncture end 34 capable of puncturing the elastomeric end of the specimen tube 80 and expelling the fluid into the specimen tube 80. The retracting holder 30 passes fluid from the vein through the needle 10 and the fluid expelling portion 32 into the specimen tube 80. The specimen tube can be removed and another used to allow for multiple samples to be taken from one site.

Figure 8:
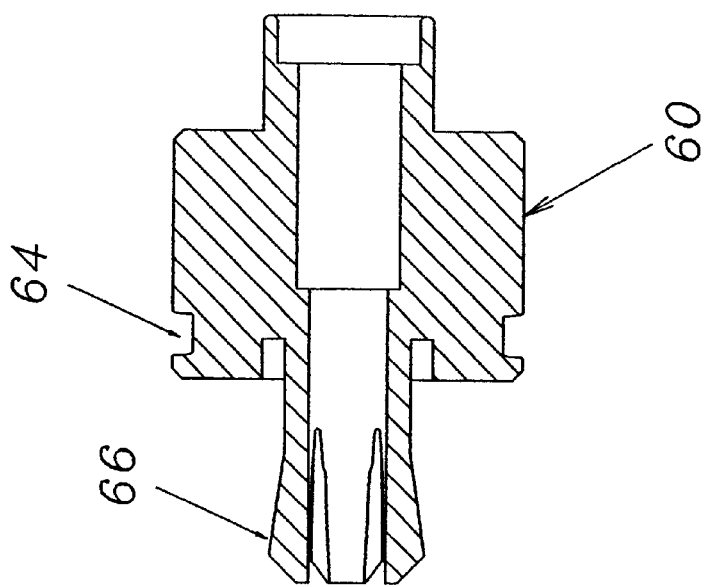
FIG. 8 is a cross-sectional view of the collet and inner barrel.
Figure 7:
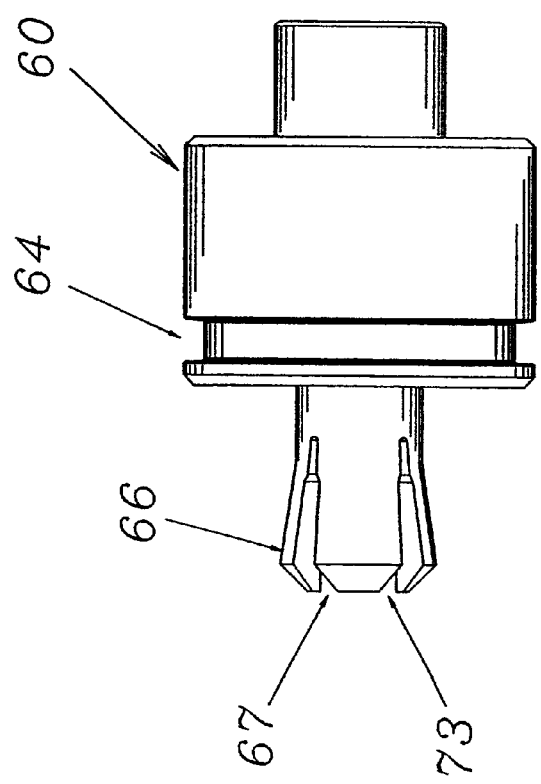
FIG. 7 is a plan view of the collet and inner barrel.

Details of the collet 66 of this embodiment are shown in FIGS. 6, 7 and 8. The collet includes a plurality of slots 67 which allow for expansion and contraction of the collet as the exterior funnel shape of the collet is urged forwardly and rearwardly through the forward opening 72 in outer tube 50 of the fluid collection tube holding device 20. The slots 67 are larger at the forward ends 73 of the collet and taper rearwardly. The forward ends 73 of the slots 67 are sized to accommodate the wedges 74. When the collet 66 is urged rearwardly with respect to the outer barrel 50 by a short spring 68, the slots 67 in the collet forward end are forced into a closed position, without interference from wedges 74, reducing the diameter of the collet and clamping the holder 30. This clamping and retention of the holder is helped by the trapped edge 31 which is present of the exterior of the holder 30. The collet 66 clamps onto the holder just behind the trapped edge. The trapped edge 31 is shown as an annular element in this embodiment, however, it can take on any shape which binds against the restricting edges of the collet 66 and retains the holder 30 in the forward end of the inner barrel 60.

The retracting holder 30 is biased rearwardly by long spring 38 which pushes on the end cap 35 of the holder. To release the holder 30, the collet 66 is expanded by forward movement of the collet 66 in response to contact with the inner barrel forward end 64, and the forward end 44 of the plunger. The forward movement of the collet 66 frees the collet from the constriction of the opening 72 and engages the narrowed portions 75 of the slots 67 with the wedges 74 to force the collet to expand clear of the lip on the retracting holder 30.

To collect a sample, the user inserts the needle 10 of the assembly into a vein. The elastomeric end of the specimen tube 80 is introduced into the rearward end of the inner barrel 60. The specimen tube 80 is fully inserted into the inner barrel 60 until the puncture end 34 of the fluid expelling portion 32 punctures the elastomeric end of the specimen tube 80. The blood enters the needle 10 of the retracting holder 30 through the fluid expelling portion 32 and into the specimen tube 80. After the user has collected the quantity needed, the specimen tube 80 is removed from the inner barrel 60. Another specimen tube can be inserted if multiple samples are needed.

Figure 3:
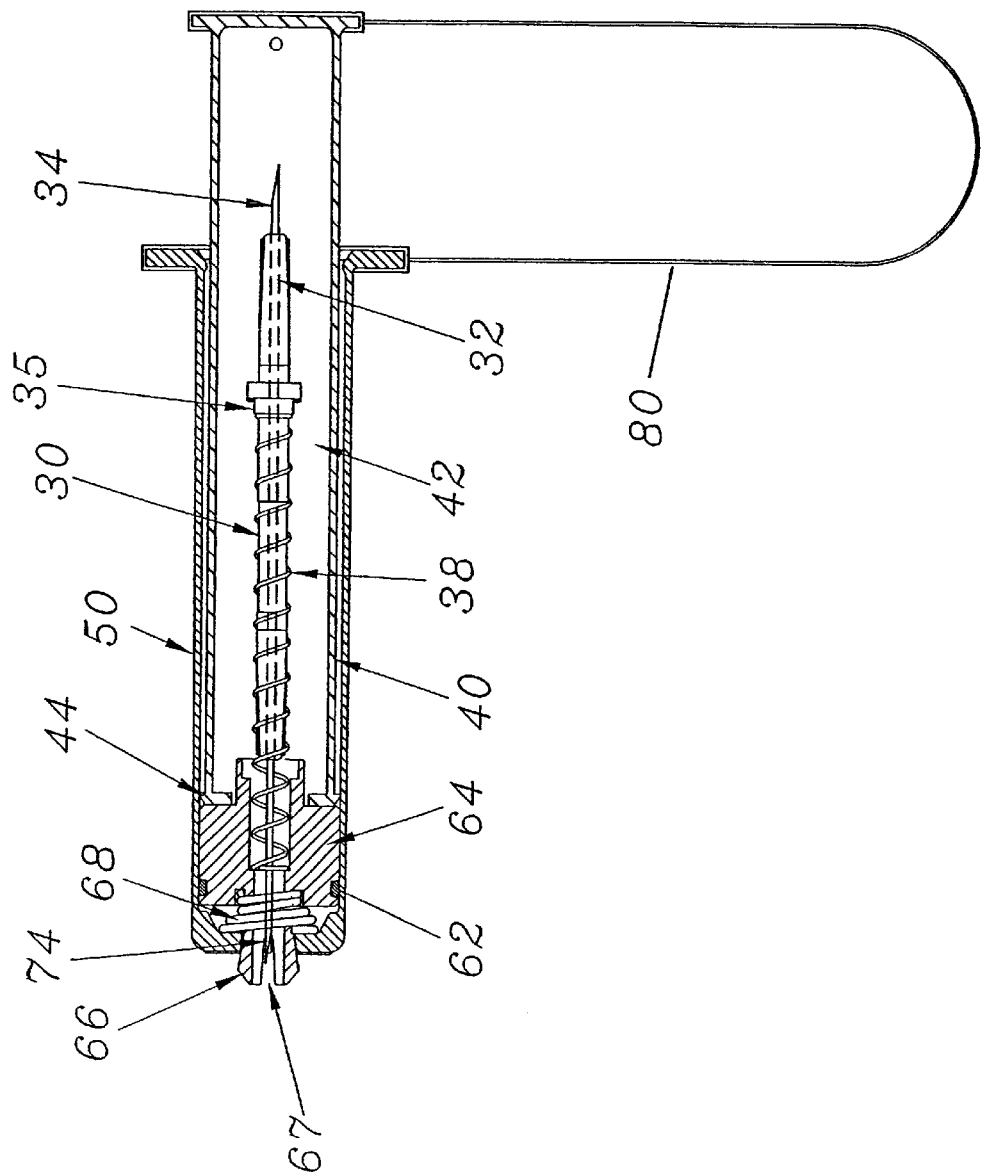
FIG. 3 is a partial sectional side view of the fluid collection assembly according to the present invention shown in the retracted position.

When the user has removed the specimen tube, the plunger 40 is inserted into the space between the inner barrel 60 and outer barrel 50. The user pushes until the annular plunger end 44 urges against the inner barrel 60 which in turn pushes the collet 66 forward. By pushing forward, the collet 66 expands and the holder 30 disengages from the collet 66 and the holder 30 is propelled rearwardly into the tubular body of the inner barrel 60. The needle 10 is then disabled with the needle trapped within the assembly as shown in FIG. 3. The plunger 40 can be connected to the outer barrel 50 by a tether 80 placed on the rearward ends of each. This prevents misplacement of the plunger.

Figure 4:
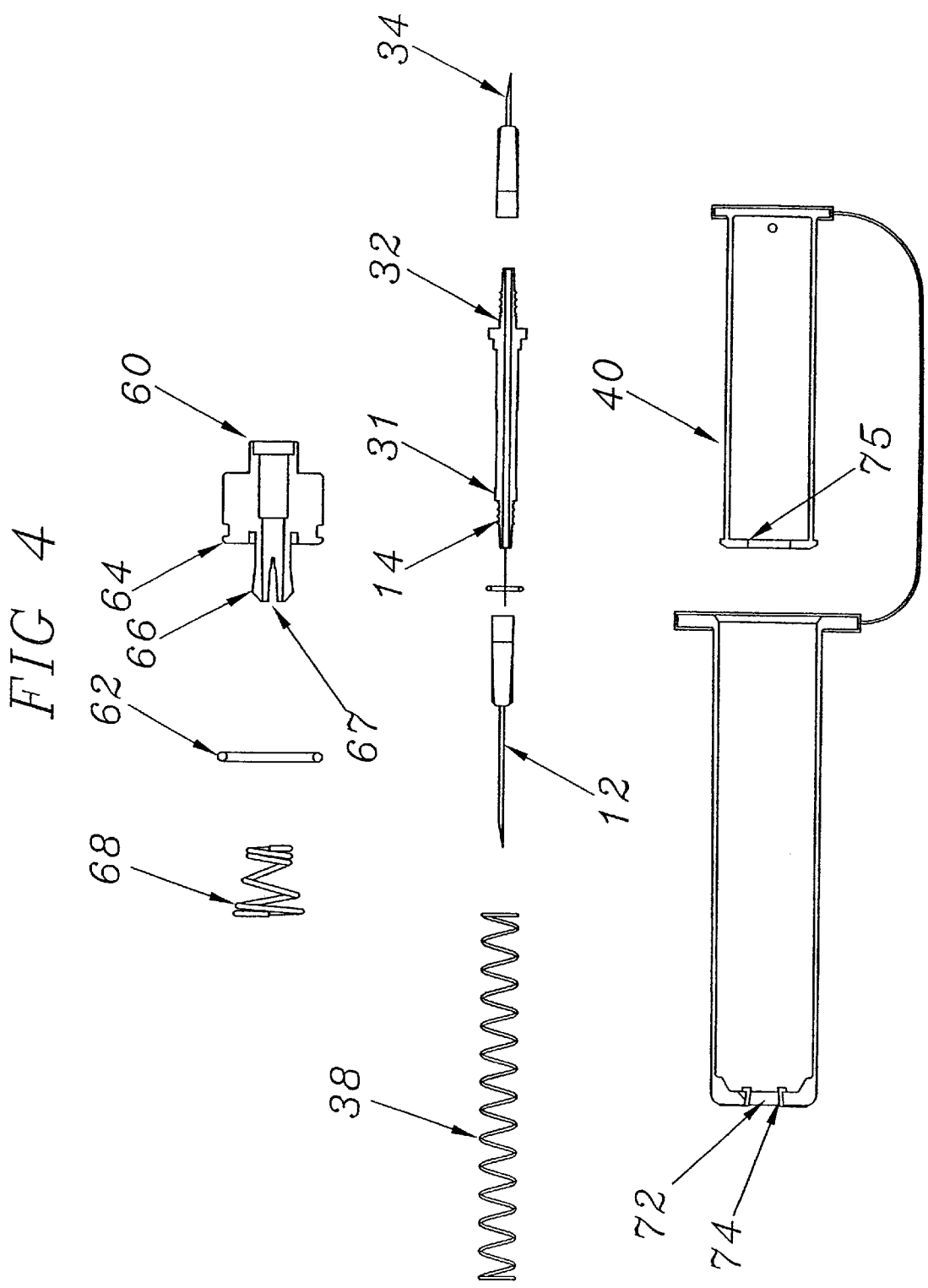
FIG. 4 is an exploded view of the fluid collection assembly sequence of the component parts with the forward end of the barrel enlarged.
Figure 5:
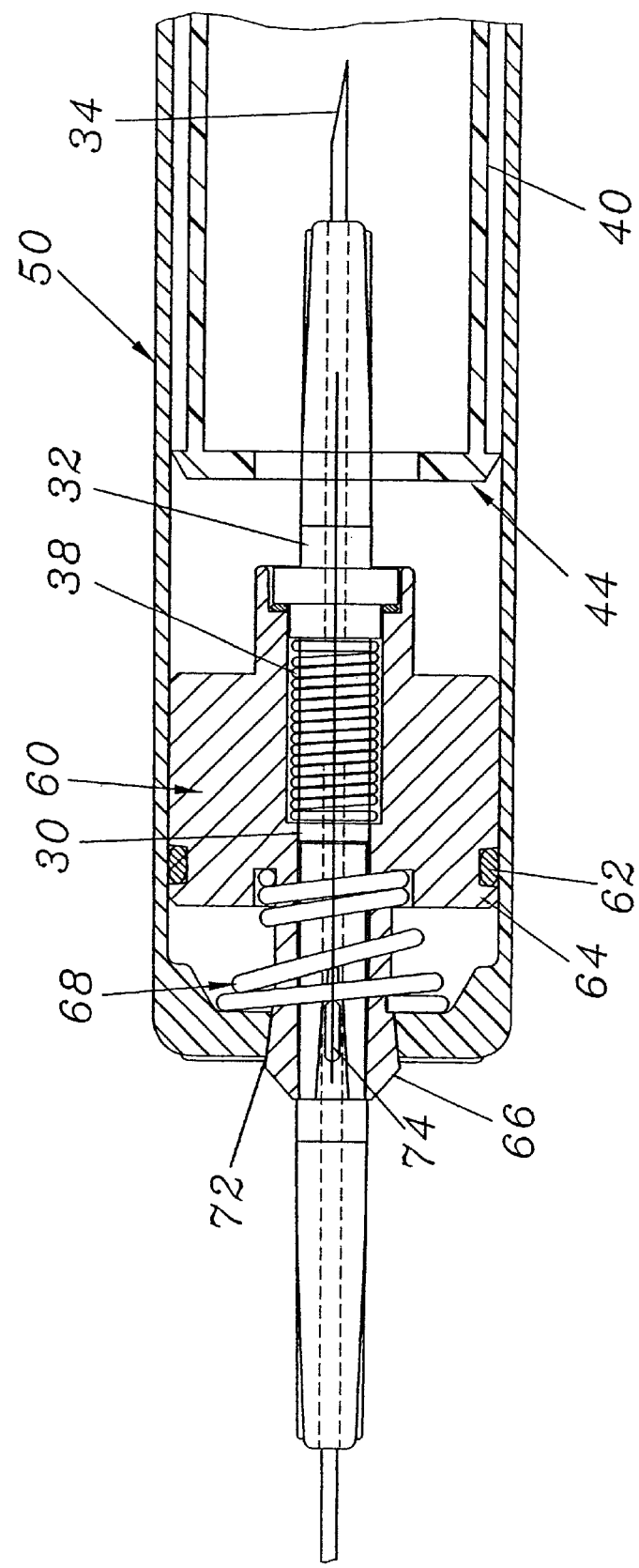
FIG. 5 is an enlarged partial sectional view of the forward end of the assembly according to the present invention.

The assembly sequence of the present invention is shown in FIG. 4. The holder 30 and the associated long spring 38 are inserted into the inner barrel 60 which is comprised of a forward end 64 and seal 62 and collet 66. The inner barrel 60 and the short spring 68 are loaded into the outer tube 50 followed by the insertion of the assembled holder 30. The holder is inserted until engagement of the collet occurs forward followed by the insertion of the assembled plunger. The entire assembly includes four polymer plastic molded parts, namely the plunger, outer and inner barrels, the holder and seal, and two springs. The seal can also be a polymer and consequently be molded together with the respective inner barrel and holder as desired. By virtue of the comparatively few numbers of parts and their simplicity in execution, the present assembly and retractable needle combination can be readily and economically manufactured.

It is to be understood that while I have illustrated and described certain forms of my invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

What is claimed is:

1. An assembly for use with a blood collection tube, said blood collection tube having a closed end and an open end sealed by an elastomeric material, said assembly comprising a tube holder with an outer barrel for slidably receiving the blood collection tube, said outer barrel having a forward end and rearward end, said forward end of said outer barrel having an opening, an inner barrel having a forward end and an open rearward end slidably inserted into the rearward end of said outer barrel, said inner barrel having an expandable collet mounted on said forward end thereof, spring means positioned between said outer barrel and inner barrel so as to bias said inner barrel rearwardly with respect to said outer barrel, said collet extending through said forward end of said outer barrel opening and engaging said opening in said forward end of said outer barrel, said opening constricting said collet as said collet is biased rearwardly through said opening, a needle retractor having a forward end extending through said collet and adapted to receive a needle slidably received in said inner barrel, said needle retractor having a shoulder trap engaging said restricted collet, said needle retractor having a tubular body and a rearward end carrying a puncture end for penetrating the elastomeric seal of said blood collection tube, second spring means for biasing said needle retractor rearwardly positioned between said inner barrel and said needle retractor, and a tubular plunger having an annular forward end and a rearward end, said plunger adapted for insertion into the rearward end of said outer barrel, said annular forward end of said plunger adapted to contact said inner barrel whereby forward movement of said inner barrel with respect to said outer barrel releases said needle retractor rearwardly into said inner barrel.

2. An assembly as in claim 1 further comprising a vent in said rearward end portion of said plunger.

3. An assembly as in claim 2 further comprising a needle connected to the forward end of said needle retractor element.

4. An assembly as in claim 2 further comprising screw attachment means for attaching said needle to a forward end of said needle retractor.

5. An assembly as in claim 2 wherein said spring means comprises a coil spring.

6. An assembly as in claim 2 wherein said second spring means comprises a coil spring.

7. An assembly as in claim 2 wherein said forward end of said inner barrel is enlarged to form a first seal between said outer barrel portion and said inner barrel.

8. An assembly as in claim 7 wherein said first seal means comprises a separate O-ring type seal mounted on said forward end of said inner barrel.

9. An assembly as in claim 2 wherein said expandable collet has a funnel shaped exterior and includes slots which enable expansion in contraction of the longitudinal passageway located within said collet.

10. An assembly as in claim 9 wherein said opening in said forward end of said outer barrel has at least one wedge element, said wedge element engaging said slots in said collet to force said collet to expand.

11. An assembly as in claim 2 wherein said. outer barrel and said plunger are connected with a tether, said tether connecting said rearward end of said outer barrel said rearward end or said plunger.

12. An assembly as in claim 2 with means within said inner barrel for guiding and supporting the blood collection tube.

13. A method for collecting fluid samples comprising:

A) providing a blood collection tube having a closed end and an open end sealed with an elastomeric material;

B) providing an assembly having a tube holder with an outer barrel for slidably receiving the blood collection tube, said outer barrel having a forward end and a rearward end, said forward end formed with an opening therein, an inner barrel having a forward end and an open rearward end slidably inserted into the rearward end of said outer barrel, said inner barrel having an expandable collet mounted on said forward end thereof, spring means positioned between said outer barrel and inner barrel so as to bias said inner barrel rearwardly with respect to said outer barrel, said collet extending through said forward end of said outer barrel opening and engaging said opening in said outer barrel, said opening constricting said collet as said collet is biased rearwardly through said opening, an elongated needle retractor having a through bore slidably extending through said collet and said inner barrel, one end of said needle retractor adapted to receive a needle, said needle retractor having a shoulder trap engaging said restricted collet, said needle retractor having a puncture means for penetrating said elastomeric seal of said blood collection tube on the other end, a second spring biasing said needle retractor rearwardly positioned between said inner barrel and said needle retractor, and a tubular plunger having an annular forward end and a rearward end,; and C) inserting said needle into a patient, inserting said open end of said blood collection tube into said outer barrel, penetrating said elastomeric seal with said puncture means, collecting said sample in said blood collection tube, removing said blood collection tube from said outer barrel, inserting said plunger in said outer barrel, advancing said annular forward end of said plunger over said inner barrel into contact with said forward end of said inner barrel, continuing advancing said plunger compressing said spring means and expanding said collet out of contact with said shoulder trap, said needle retractor sliding into said inner barrel in response to the bias of said second spring means carrying said needle within said needle holder.

\* \* \* \* \*